US006030815A

United States Patent [19]
DeFrees et al.

[11] Patent Number: 6,030,815
[45] Date of Patent: *Feb. 29, 2000

[54] ENZYMATIC SYNTHESIS OF OLIGOSACCHARIDES

[75] Inventors: Shawn DeFrees, San Marcos; Robert J. Bayer, San Diego; Murray Ratcliffe, Carlsbad, all of Calif.

[73] Assignee: Neose Technologies, Inc., Horsham, Pa.

[*] Notice: This patent is subject to a terminal disclaimer.

[21] Appl. No.: 08/628,543

[22] Filed: Apr. 10, 1996

Related U.S. Application Data

[63] Continuation-in-part of application No. 08/419,659, Apr. 11, 1995, Pat. No. 5,876,980.

[51] Int. Cl.[7] .............................. C12P 19/18; C12P 19/12; C12P 19/04; C12P 19/00
[52] U.S. Cl. ............................... 435/97; 435/84; 435/100; 435/101; 536/4.1; 536/17.2; 536/18.5; 536/123.1; 536/123.13; 536/123
[58] Field of Search .............................. 435/97, 100, 101, 435/84; 536/4.1, 17.2, 18.5, 123.1, 123.13, 123

[56] References Cited

U.S. PATENT DOCUMENTS

| | | |
|---|---|---|
| 5,164,374 | 11/1992 | Rademacher . |
| 5,278,299 | 1/1994 | Wong . |
| 5,288,637 | 2/1994 | Roth . |
| 5,352,670 | 10/1994 | Venot . |
| 5,374,655 | 12/1994 | Kasham . |
| 5,728,554 | 3/1998 | Bayer et al. ............... 435/97 |

FOREIGN PATENT DOCUMENTS

| | | |
|---|---|---|
| WO 92/16640 | 10/1992 | WIPO . |
| WO 94/26760 | 11/1994 | WIPO . |
| WO 9425615 | 11/1994 | WIPO . |
| WO 96/32491 | 10/1996 | WIPO . |
| WO 96/32492 | 10/1996 | WIPO . |
| WO/94/25614 | 10/1996 | WIPO . |

OTHER PUBLICATIONS

1990 Sigma Chemical Company Catalogue. pp. 217, 461, 729.
Carlson, Don M., et al. (1973) "Synthesis of Sialyl Lactose By A Sialyltransferase From Rat Mammary Gland", *The Journal of Biological Chemistry*, 248(16):5742–5750.
Ito, et al. (1993) *Pure Appl. Chem.* 65:753.
Van den Eijnden, et al. (1981) *J. Biol. Chem.*, 256:3159.
Weinstein, et al. (1982) *J. Biol. Chem.*, 257:13845.
Wen et al. (1992) *J. Biol. Chem.*, 267:21011.
Rearick, et al. (1979) *J. Biol. Chem.*, 254:4444.
Gillespie, et al. (1992) *J. Biol. Chem.*, 267:21004.
Kurosawa, et al. (1994) *Eur. J. Biochem.*, 219:375–381.
Gross, et al. (1987) *Eur. J. Biochem.*, 168:595.
Vijay, et al. (1975) *J. Biol. Chem.*, 250 (1):164.
Zapata, et al. (1989) *J. Biol. Chem.*, 264:(25):14769.
Higa, et al. (1985) *J. Biol. Chem.*, 260(15):8838.
Vann, et al. (1987) *J. Biol. Chem.*, 262:17556.
Shames, et al. (1991) *Glycobiology*, 1:187.
Nunez, H.A., et al. (1976) "The Metal Ion Catalyzed Decomposition of Nucleoside Diphosphate Sugars", *Biochemistry*, 15(17):3843–3847.
Wong, Chi–Huey, et al. (1992) "Regeneration of Sugar Nucleotide for Enzymatic Oligosaccharide Synthesis: Use of Gas–1–Phopsphate Uridyltransferase in the Regeneration of UDP–Galactose, UDP–2–Deoxygalactose, and UDP–Talactosamine", *J. Org. Chem.*, 57(16):4343–4344.
Kurosawa, et al. (1993) *J. Biol. Chem.*, 268:26273–78.
Livingston, et al. (1993) *J. Biol. Chem.*, 268:11504.
Simon, et al. (1988) *J. Am. Chem. Soc.*, 110:7159.
Dabkowski, et al. (1993) *Transplant Proc.*, 25:2921.
Yamamoto, et al. (1990) *Nature*, 345:229–233.
Auge, et al. (1990) *Carbohydrate Research* 200:257–268.
Auge, et al. (1986) *Carbohydrate Research* 151:147–156.
Ichikawa, et al. (1991) *J. Am. Chem. Soc.* 113:4698–4700 and 113 (16):6300–6302 (1991).
DeLuca, et al. (1995) *J. Am. Chem. Soc.* 117:5869–5870.
David, Serge et al. (1987) "Immobolized Enzymes n Preparative Carbohydrate Chenistry", *Pure & Appl. Chem.*, 59 (11):1501–1508.
Burczak, J.D. et al. (1984) "Characterization of a CMP–Sialic Acid: Lactosylceramide–Sialyl Transferase Activity in Cultured Hamster Cells" vol. 804, No. 4 Biophys. Acta., 442–449.

*Primary Examiner*—Francisco Prats
*Attorney, Agent, or Firm*—Townsend and Townsend and Crew LLP

[57] ABSTRACT

The present invention provides improved methods for the preparation of sialyl galactosides. The methods use sialyl transferase cycle in which the reaction conditions are optimized to provide increased yields.

26 Claims, 2 Drawing Sheets

ENZYMATIC SYNTHESIS OF OLIGOSACCHARIDES

CROSS-REFERENCE TO RELATED APPLICATIONS

This is a continuation in part of U.S. Ser. No. 08/419,659, filed Apr. 11, 1995 now U.S. Pat. No. 5,876,980, it is also related to U.S. Ser. No. 08/419,669, filed Apr. 11, 1995 now U.S. Pat. No. 5,728,554 and U.S. Ser. No. 08/628,545 filed Apr. 10, 1996 now U.S. Pat. No. 5,922,577.

FIELD OF THE INVENTION

The present invention relates to the synthesis of oligosaccharides. In particular, it relates to improved enzymatic syntheses of such compounds in a single vessel using readily available starting materials.

BACKGROUND OF THE INVENTION

Increased understanding of the role of carbohydrates as recognition elements on the surface of cells has led to increased interest in the production of carbohydrate molecules of defined structure. For instance, compounds comprising the oligosaccharide moiety, sialyl lactose, have been of interest as neutralizers for enterotoxins from bacteria such as *Vibrio cholerae, Eschericia coli,* and Salmonella (see, e.g., U.S. Pat. No. 5,330,975). Sialyl lactose has also been investigated for the treatment of arthritis and related autoimmune diseases. In particular, sialyl lactose is thought to inhibit or disrupt the degree of occupancy of the Fc carbohydrate binding site on IgG, and thus prevent the formation of immune complexes (see, U.S. Pat. No. 5,164,374). Recently, sialylα(2,3)galactosides, sialyl lactose and sialyl lactosamine have been proposed for the treatment of ulcers, and Phase I clinical trials have begun for the use of the former compound in this capacity. See, Balkonen, et al., *FEMS Immunology and Medical Microbiology* 7:29 (1993) and BioWorld Today, p. 5, Apr. 4, 1995. In addition, sialyl lactose is useful as food supplement, for instance in baby formula.

Because of interest in making desired carbohydrate structures, glycosyltransferases and their role in enzyme-catalyzed synthesis of carbohydrates are presently being extensively studied. These enzymes exhibit high specificity and are useful in forming carbohydrate structures of defined sequence. Consequently, glycosyltransferases are increasingly used as enzymatic catalysts in synthesis of a number of carbohydrates used for therapeutic and other purposes.

In the application of enzymes to the field of synthetic carbohydrate chemistry, the use of sialyltransferases for enzymatic sialylation offers advantages over chemical methods due to the virtually complete stereoselectivity and linkage specificity offered by the enzymes (Ito et al., *Pure Appl. Chem.,* 65:753 (1993) U.S. Pat. Nos. 5,352,670, and 5,374,541).

Improved methods for enzymatic synthesis of sialylated carbohydrate compounds would advance the production of a number of beneficial compounds. The present invention fulfills these and other needs.

SUMMARY OF THE INVENTION

The present invention provides methods for the preparation of sialyl saccharides, preferably sialyl galactosides. In particular, the methods comprise (a) providing a reaction medium comprising:
(i) a sialyltransferase;
(ii) a catalytic amount of a CMP-sialic acid synthetase;
(iii) a sialic acid;
(iv) an acceptor for the sialyltransferase, preferably having a galactosyl unit;
(v) CTP; and
(vi) a soluble divalent metal cation; and (b) supplementing the soluble divalent metal cation to achieve a concentration of the soluble divalent metal cation in said reaction medium of between about 1 mM and about 75 mM, for a period of time sufficient to sialylate the acceptor. Preferably, the concentration of the soluble divalent metal cation is maintained between about 2 mM and about 75 mM. Supplementing can be carried out either discontinuously or continuously.

In preferred embodiments the reaction medium further comprises a CMP-sialic acid recycling system comprising at least 2 moles of phosphate donor per each mole of sialic acid, and catalytic amounts of an adenine nucleotide, a kinase capable of transferring phosphate from the phosphate donor to nucleoside diphosphates, and a nucleoside monophosphate kinase capable of transferring the terminal phosphate from a nucleoside triphosphate to CMP. For those embodiments in which a CMP-sialic acid recycling system is not used, the reaction medium will preferably further comprise a phosphatase.

The divalent metal cation used in the methods can be $Mn^{++}$, $Mg^{++}$, $Ca^{++}$, $Co^{++}$, $Zn^{++}$ or combinations thereof. Typically the cation is Mn++. The sialyltransferase is typically α(2,3)sialyltransferase or α(2,6)sialyltransferase. Preferred sialic acids include 5-N-acetylneuraminic acid. For the production of sialyl lactose, the acceptor is lactose.

The invention also provides sialyl lactose preparations of very high purity. These products are particularly useful in various therapeutic and diagnostic applications.

DETAILED DESCRIPTION OF THE INVENTION

The present invention provides methods for production of sialyl oligosaccharides useful in various diagnostic and therapeutic applications. The methods rely on the use of sialyl transferase to catalyze the addition of a sialic acid residue to a substrate comprising a galactosyl residue at the non-reducing end of an oligosaccharide or carbohydrate moiety on a biomolecule. Thus, the products of the methods of the invention are referred to here as sialyl galactosides. Biomolecules as defined here include but are not limited to biologically significant molecules such as proteins (e.g., glycoproteins), and lipids (e.g., glycolipids, phospholipids, sphingolipids and gangliosides). Thus, the substrate for the sialyl transferases used in the methods of the invention can be any molecule comprising a galactosyl residue that can be sialylated by these enzymes. As explained below, a preferred substrate is lactose which is used to produce sialyl lactose.

The following abbreviations are used herein:

Ara=arabinosyl;
Fru=fructosyl;
Fuc=fucosyl;

Gal=galactosyl;

GalNAc=N-acetylgalacto;

Glc=glucosyl;

GlcNAc=N-acetylgluco;

Man=mannosyl; and

NeuAc=sialyl (N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (i.e., Gal), followed by the configuration of the glycosidic bond ($\alpha$ or $\beta$), the ring bond (1 or 2), the ring position of the reducing saccharide involved in the bond (2, 3, 4, 6 or 8), and then the name or abbreviation of the reducing saccharide (i.e., GlcNAc).

Embodiments of the Invention

A number of glycosyl transferase cycles (for example, the sialyltransferase cycles depicted in FIG. 1) are useful for the preparation of oligosaccharides. See, U.S. Pat. No. 5,374,541 and WO 9425615 A. These enzyme cycles produce at least one mole of inorganic pyrophosphate for each mole of product formed and are typically carried out in the presence of a divalent metal ion. The metal ion is a cofactor for at least one of the enzymes in each of the cycles.

In the sialyltransferase cycle (FIG. 1), an enzyme with an absolute requirement for divalent metal cations is CMP-NeuAc synthetase (see, Kean, et al., METHODS IN ENZYMOLOGY 8:208–215 (1966)). Other enzymes in this sialyltransferase cycle with an absolute requirement for divalent metal ions are pyruvate kinase and myokinase (see, Villafranca, et al., THE ENZYMES, XX:63–94 (1992)).

Figure 2:
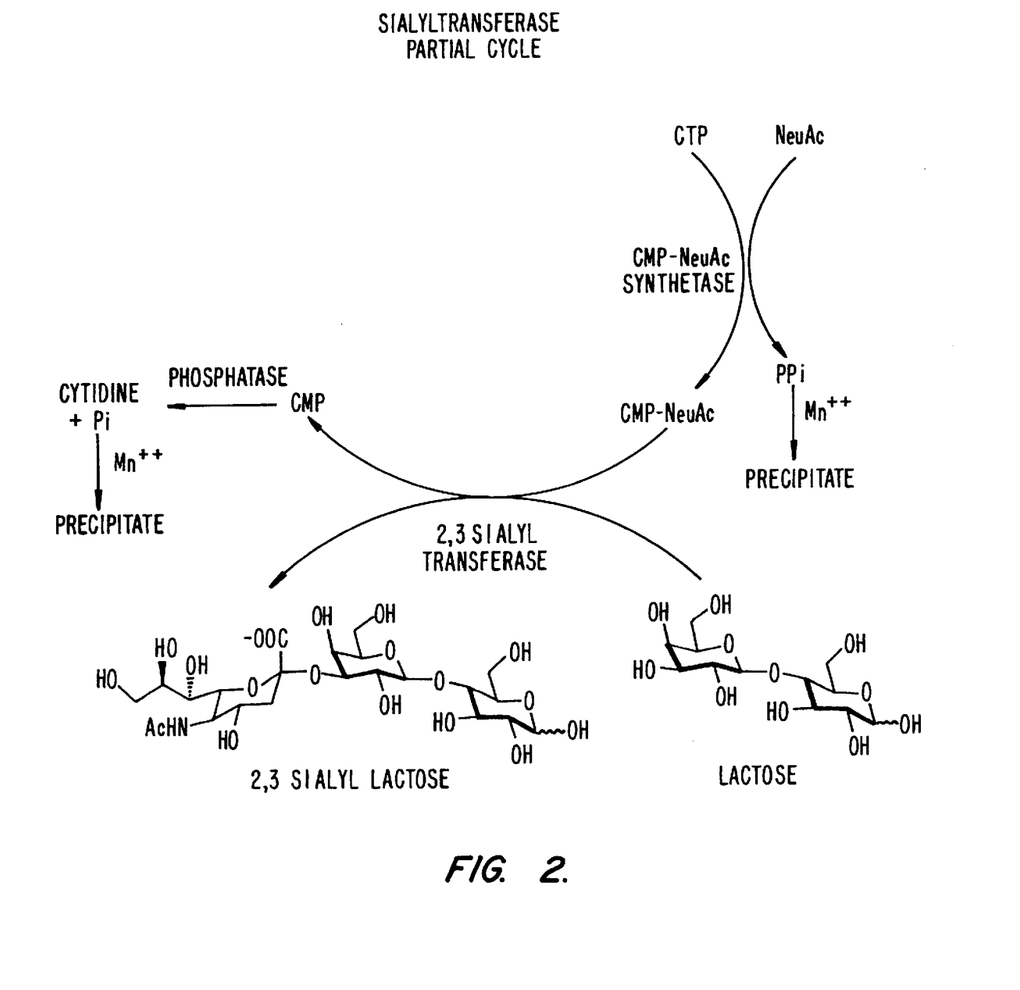
FIG. 2 illustrates a partial cycle using sialyl transferase which can be optimized by supplementation of divalent metal ions.

A partial cycle or stoichiometric reaction comprising a sialyltransferase, CMP-NeuAc synthetase, a suitable acceptor, sialic acid, CTP and a suitable divalent metal cation can also be carried out (see FIG. 2). In this reaction, inorganic pyrophosphate is generated by the CMP-NeuAc synthetase reaction.

For each of the sialyl transferase cycles or partial cycles, the combination of pyrophosphate and some divalent metal cations produces a complex of particularly low solubility. This, in turn, results in reduced amounts of metal ions present in solution and a corresponding decrease in the overall turnover rates for those enzymes which require the metal ion cofactors. This problem is particularly acute when the enzymatic glycosylations are scaled-up for manufacturing purposes. For such large scale synthesis, economic and facility considerations require that the reactions be carried out in as concentrated a solution as feasible to reduce the raw materials requirements, maintain reasonable vessel size, and reduce the quantity of aqueous solvent to be removed. At higher concentrations of reactants, the concentration of phosphate or pyrophosphate generated is proportionally greater.

Additionally, for the sialyltransferase partial cycle, if sufficient CTP and sialic acid are present, the reaction proceeds until either the divalent metal cation is depleted, or inhibitory CMP builds up to a sufficient level. The inhibitory nucleotide can be removed by treatment with a suitable phosphatase which generates Pi. However, this serves to further deplete the divalent metal cation.

One potential solution to this problem involves beginning with large concentrations of metal ion cofactors. However, the use of large concentrations of metal ion cofactors has proven detrimental to both the galactosyltransferase and sialyltransferase cycles. Alternatively, others have incorporated inorganic pyrophosphatase into the reaction medium in an attempt to drive the reaction cycles to completion by removal of pyrophosphate. Nevertheless, complexes of limited solubility are formed between the orthophosphate produced by inorganic pyrophosphatase and the metal ion cofactor, with the effective reduction in metal ion concentrations.

Accordingly, the present invention provides in one aspect a method for sialylating an acceptor sugar. In this method a medium (typically an aqueous solution) containing a soluble divalent metal cation is provided which also contains the acceptor sugar, a sialic acid, CMP-sialic acid synthetase, CTP and a sialyltransferase. The concentration of the soluble divalent metal cation in the reaction medium is supplemented during the formation of the glycosidic linkage. This addition of soluble divalent metal cation serves to replenish a portion of the soluble metal cation which is lost by precipitation and thereby achieves or maintains a concentration of between about 1 mM and about 75 mM, preferably between about 5 mM and about 50 mM and more preferably between about 10 and about 40 mM. In one preferred embodiment, the medium further comprises a phosphatase.

By monitoring the metal ion concentration in the reaction medium and supplementing the medium by additional amounts of divalent metal ions, the reaction can be driven to substantial completion within a suitable timeframe. As used herein, terms such as "substantial completion" and "to sialylate the acceptor" and the like are used to indicate reactions which are carried to at least 90% completion, more preferably 95% completion and still more preferably 98% completion, as determined by tlc or proton NMR. Additionally, if more than one glycosyltransferase is used, consecutive cycles can be carried out in the same reaction vessel without isolation of the intermediate product. Moreover, by removing the inhibitory pyrophosphate, the reaction cycles can be run at substantially higher substrate (acceptor) concentration. Preferred divalent metal ions for use in the present invention include $Mn^{++}$, $Mg^{++}$, $Co^{++}$, $Ca^{++}$, $Zn^{++}$ and combinations thereof. More preferably, the divalent metal ion is $Mn^{++}$.

In one group of preferred embodiments, the aqueous medium contains, in addition to the components described above, a CMP-sialic acid recycling system comprising at least 2 moles of phosphate donor per each mole of sialic acid, and catalytic amounts of a nucleoside triphosphate, a kinase capable of transferring phosphate from the phosphate donor to nucleoside diphosphates, and a nucleoside monophosphate kinase capable of transferring the terminal phosphate from a nucleoside triphosphate to CMP.

An $\alpha(2,3)$sialyltransferase, often referred to as the sialyltransferase, is the principal enzyme utilized herein in the production of sialyl lactose. This enzyme transfers sialic acid (NeuAc) to a Gal with the formation of an $\alpha$-linkage between the two saccharides. Bonding (linkage) between the saccharides is between the 2-position of NeuAc and the 3-position of Gal.

An exemplary $\alpha(2,3)$sialyltransferase referred to as $\alpha(2,3)$sialtransferase (EC 2.4.99.6) transfers sialic acid to the non-reducing terminal Gal of a Gal$\beta$1→3Glc disaccharide or glycoside. See, Van den Eijnden et al., J. Biol. Chem., 256:3159 (1981), Weinstein et al., J. Biol. Chem., 257:13845 (1982) and Wen et al., J. Biol. Chem., 267:21011 (1992). Another exemplary $\alpha$-2,3-sialyltransferase (EC 2.4.99.4) transfers sialic acid to the non-reducing terminal Gal of the disaccharide or glycoside. See, Rearick et al., *J. Biol. Chem.,* 254:4444 (1979) and Gillespie et al., *J. Biol. Chem.,* 267:21004 (1992). Further exemplary enzymes include Gal-β-1,4-GlcNAc α-2,6 sialyltransferase (See, Kurosawa et al. *Eur. J. Biochem.* 219: 375–381 (1994)).

A second principle enzyme used in the present methods is CMP-sialic acid synthetase. This enzyme is preferably utilized in the CMP-sialic acid regenerating (recycling) system, discussed in detail hereinafter. CMP-sialic acid synthetase can be isolated and purified from cells and tissues containing the synthetase enzyme by procedures well known in the art. See, for example, Gross et al., *Eur. J. Biochem.,* 168:595 (1987), Vijay et al., *J. Biol. Chem.,* 250(1):164 (1975), Zapata et al., *J. Biol. Chem.,* 264(25):14769 (1989) and Higa et al., *J. Biol. Chem.,* 260(15):8838 (1985). The gene for this enzyme has also been sequenced. See, Vann et al., *J. Biol. Chem.,* 262:17556 (1987). An overexpression of the gene, has also been reported for use in a gram scale synthesis of CMP-NeuAc. See, Shames et al., *Glycobiology,* 1:187 (1991). This enzyme is also commercially available.

A sialic acid is also required. A contemplated sialic acid includes not only sialic acid itself (5-N-acetylneuraminic acid; 5-N-acetylamino-3,5-dideoxy-D-glycero-D-galacto-2-nonulosonic acid; NeuAc, and sometimes also abbreviated AcNeu or NANA), but also 9-substituted sialic acids such as a 9-O-$C_1C_6$ acyl-NeuAc like 9-O-lactyl-NeuAc or 9-O-acetyl-NeuAc, 9-deoxy-9-fluoro-NeuAc and 9-azido-9-deoxy-NeuAc. The synthesis and use of these compounds in a sialylation procedure is disclosed in international application WO 92/16640, published Oct. 1, 1992. Other suitable sialic acids include N-glycolyl neuraminic acid, 5-hydroxyneuraminic acid, 5-CbzNH, 5-$CH_3$OC(O)NH neuraminic acid (Shames et al. *Glycobiol.* 1:187 (1991)), and 5-N-acyl neuraminic acid.

The reaction mixture will also contain an acceptor for the sialyltransferase, preferably having a galactosyl unit. Suitable acceptors, include, for example, Galβ1→3GalNAc, lacto-N-tetraose, Galβ1→3GlcNAc, Galβ1→3Ara, Galβ1→6GlcNAc, Galβ1→4Glc (lactose), Galβ1→4Glcβ1-O$CH_2CH_3$, Galβ1→4Glcβ1-O$CH_2CH_2CH_3$, Galβ1→4Glcβ1-O$CH_2C_6H_5$, Galβ1→4GlcNAc, Galβ1-O$CH_3$, melibiose, raffinose, stachyose and lacto-N-neotetraose.

Figure 1:
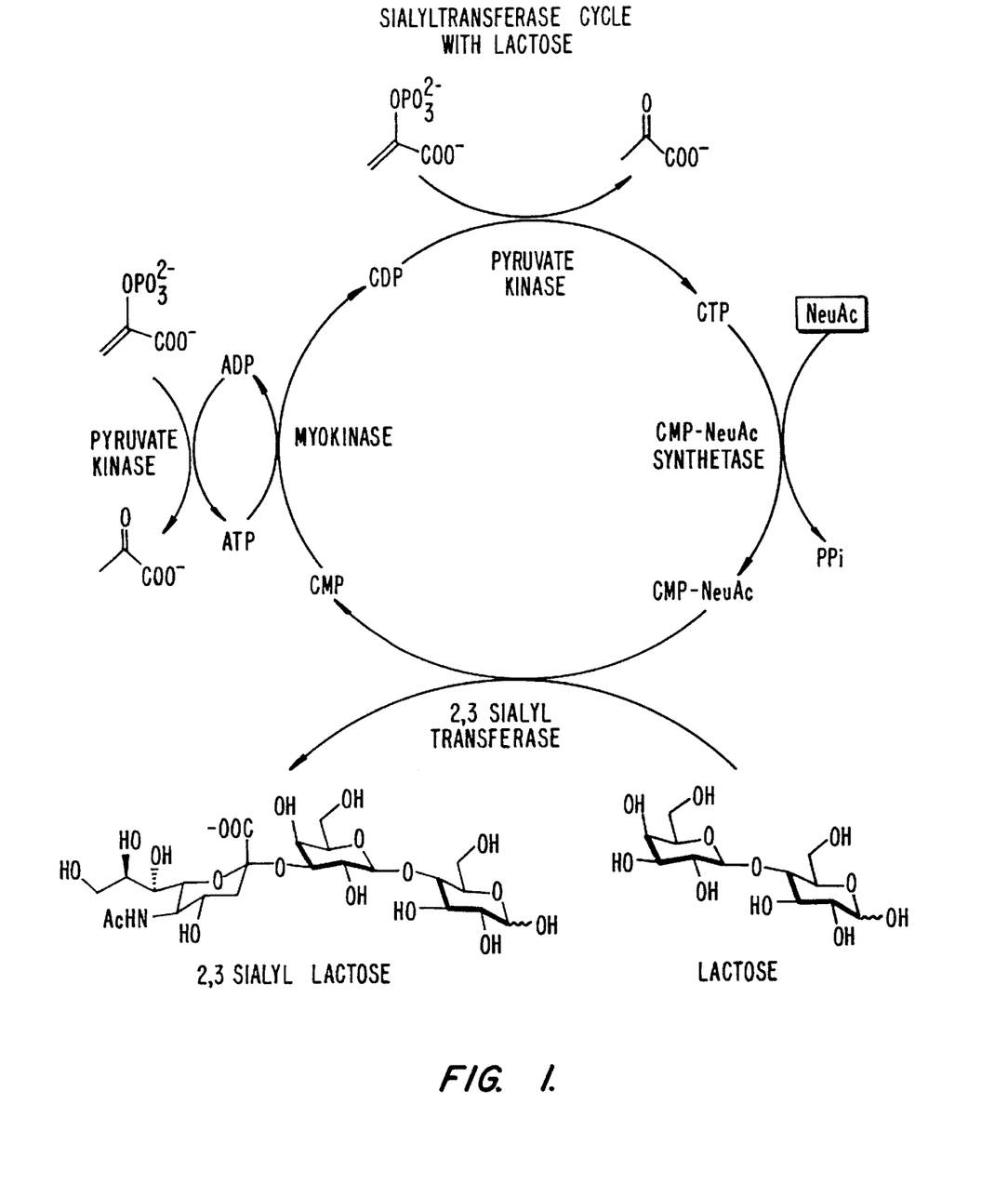
FIG. 1 illustrates a sialyl transferase cycle of the invention

The CMP-sialic acid recycling system utilizes CMP-sialic acid synthetase as noted previously. As shown in FIG. 1, CMP-sialic acid (shown in FIG. 1 as CMP-NeuAc) reacts with a sialyltransferase acceptor in the presence of a α(2,3)sialyltransferase to form the sialyl lactose.

The CMP-sialic acid regenerating system used in the present invention comprises cytidine monophosphate (CMP), a nucleoside triphosphate (for example adenosine triphosphate (ATP), a phosphate donor (for example, phosphoenolpyruvate or acetyl phosphate), a kinase (for example, pyruvate kinase or acetate kinase) capable of transferring phosphate from the phosphate donor to nucleoside diphosphates and a nucleoside monophosphate kinase (for example, myokinase) capable of transferring the terminal phosphate from a nucleoside triphosphate to CMP. The previously discussed α(2,3)sialyltransferase and CMP-sialic acid synthetase can also be formally viewed as part of the CMP-sialic acid regenerating system. However, because those two enzymes have already been discussed, they will not be discussed further here.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system of the present invention are used to catalyze the phosphorylation of CMP. NMK's are commercially available (Sigma Chem. Co., St. Louis, Mo.; Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated acceptor saccharide. Preferred phosphate donors are phosphoenolpyruvate (PEP) and acetyl phosphate. A particularly preferred phosphate donor is PEP.

The selection of a particular kinase for use in accordance with the present invention depends upon the phosphate donor employed. When acetyl phosphate is used as the phosphate donor, the kinase is acetate kinase. When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the stoichiometric substrates (free NeuAc or PEP) or acceptor is consumed.

Thus, in the sialylation example, CMP is converted to CDP, whose conversion is catalyzed by nucleoside monophosphate kinase or myokinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the α(2,3)sialyltransferase acceptor compound, the released CMP re-enters the regenerating system to reform CDP, CTP and CMP-sialic acid. By supplementing the divalent metal ion concentration during the course of the reaction cycles, the formed PPi or Pi can be removed from solution via precipitation. Moreover, the metal ion cofactor-dependent enzymes can operate at peak efficiency by maintaining the appropriate levels of divalent metal cations.

Pyruvate is also a byproduct and can be made use of in another reaction in which N-acetylmannosamine (ManNAc) and pyruvate are reacted in the presence of NeuAc aldolase (EC 4.1.3.3) to form sialic acid. Alternatively, advantage can be taken of the isomerization of GlcNAc to ManNAc, and the less expensive GlcNAc can be used as the starting material for sialic acid generation. Thus, the sialic acid can be replaced by ManNAc (or GlcNAc) and a catalytic amount of NeuAc aldolase. Although NeuAc aldolase also catalyzes the reverse reaction (NeuAc to ManNAc and pyruvate), the produced NeuAc is irreversibly incorporated into the reaction cycle via CMP-NeuAc catalyzed by CMP-sialic acid synthetase. In addition, the starting material, ManNAc, can also be made by the chemical conversion of GlcNAc using methods known in the art (see, e.g., Simon et al., *J. Am. Chem. Soc.* 110:7159 (1988). The enzymatic synthesis of sialic acid and its 9-substituted derivatives and the use of a resulting sialic acid in a different sialylating reaction scheme is disclosed in International application WO 92/16640, published on Oct. 1, 1992, and incorporated herein by reference.

As noted above, inorganic pyrophosphate (PPi) is a byproduct of the preparation of CMP-NeuAc. Produced PPi can feed back to inhibit other enzymes such that glycosylation is reduced. However, PPi can be complexed by divalent metal cations (e.g., $Mn^{++}$ or $Mg^{++}$) or degraded enzymatically. For instance, PPi can be removed by hydrolysis using inorganic pyrophosphatase (PPase; EC 3.6.1.1), a commercially available PPi catabolic enzyme (Sigma Chem. Co., St. Louis, Mo.; Boehringer Mannheim, Indianapolis, Ind.). Nevertheless, this enzymatic degradation also produces phosphate (Pi) which can form a precipitate with divalent metal cations. As a result, the processes of the present invention are driven to completion by supplementation of the divalent metal cation. As used herein, the term "pyrophosphate scavenger" refers to substances that serve to remove inorganic pyrophosphate from a reaction mixture of the present invention.

As explained below, the preferred method of removing PPi or Pi from the reaction mixture is to maintain divalent metal cation concentration in the medium. In particular, the cations and the inorganic phosphate produced form a complex of very low solubility. By supplementing the cations which are lost by precipitation with pyrophosphate, the rate of reaction can be maintained and the reactions can be taken to completion (i.e., 100% conversion).

Supplementing can be carried out continuously (e.g., by automation) or discontinuously. The term "to achieve a soluble divalent metal cation concentration" and other related terms are meant to refer to methods in which the divalent cation concentration generally stays within the optimal range such that the reaction cycle is not substantially inhibited. Thus, the terms specifically include methods in which the divalent cation concentration falls outside the optimal range for periods of time which do not allow the reduced cofactor levels to substantially inhibit the reaction cycle. As shown below, when cation concentration is maintained in this way, the transferase reaction cycle can be driven to completion.

The concentrations or amounts of the various reactants used in this trans-sialylation process depend upon numerous factors including reaction conditions such as temperature and pH value, and the choice and amount of acceptor saccharides to be sialylated. Because this sialylation process permits regeneration of activating nucleotides, activated donor sialic acid and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, sialic acid and enzymes are selected such that sialylation proceeds until either the acceptor or donor is consumed.

Each of the enzymes is preferably present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

Enzyme amounts or concentrations are expressed in activity Units. One activity Unit catalyzes the formation of 1 $\mu$mol of product at a given temperature (typically 37° C.) and pH value (typically 7.5) per minute. Thus, 10 Units of an enzyme is a catalytic amount of that enzyme where 10 $\mu$mols of substrate are converted to 10 $\mu$mol of product in one minute at a temperature of 37° C. and a pH value of 7.5.

A reagent which is recycled throughout the process is CMP/CDP/CTP. Thus, one can begin the reaction with any single species or combination of CMP, CDP and CTP. Inasmuch as CMP is the less expensive and most readily available of that group, CMP is typically used to start the reaction, with the amounts discussed before being those for the total amount of the species or combination used.

The above ingredients are combined by admixture in an aqueous reaction medium (solution). That medium has a pH value of about 6 to about 8. The medium is substantially devoid of chelators that bind enzyme cofactors such as $Mg^{+2}$ or $Mn^{+}2$. The selection of a medium is based on the ability of the medium to maintain pH value at the desired level. Thus, in some embodiments, the medium is buffered to a pH value of about 7.5, preferably with HEPES. If a buffer is not used, the pH of the medium should be maintained at about 6 to 8, preferably about 7.2 to 7.8, by the addition of base. A suitable base is NaOH, preferably 6 M NaOH.

The reaction medium may also comprise solubilizing detergents (e.g., Triton or SDS) and organic solvents such as methanol or ethanol, if necessary. In addition, the enzymes are preferably utilized free in solution, but can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about zero degrees C to about 45° C., and more preferably at about 20° C. to about 30° C.

The reaction mixture so formed is maintained for a period of time sufficient for the acceptor to be sialylated to form a desired sialyl galactoside (sialoside) product. Some of that product can often be detected after a few hours, with recoverable amounts usually being obtained within 24 hours. It is preferred to optimize the yield of the process, and the maintenance time is usually about 36 to about 240 hours.

The produced sialyl galactoside can be used without purification. However, it is usually preferred to recover the product. Standard, well known techniques for recovery of sialylated saccharides such as thin or thick layer chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 1000 to about 10,000 can be used to remove proteins. Nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used.

Thus, in a typical application, the oligosacharides of the invention will be retained in the membrane and contaminating salts will pass through. Using such techniques, sialyl galactosides of the invention (e.g., sialyl lactose) can be produced at essentially 100% purity, as determined by proton NMR and TLC.

The sialyl galactosides, including the sialyl lactosides, which are prepared according to the present invention will typically have the formula:

NeuAcα(2→3)Galβ(1→4)GlcX(R')β-OR

In this formula, X is O, N or NH, R' is hydrogen, alkyl or acyl from 1–18 carbons, 5,6,7,8-tetrahydro-2-naphthamido; benzamido; 2-naphthamido; 4-aminobenzamido; or 4-nitrobenzamido. R is a hydrogen, a saccharide, an oligosaccharide or an aglycon group having at least one carbon atom.

The term "aglycon group having at least one carbon atom" refers to a group —A—Z, in which A represents an alkylene group of from 1 to 18 carbon atoms optionally substituted with halogen, thiol, hydroxy, oxygen, sulfur, amino, imino, or alkoxy; and Z is hydrogen, —OH, —SH, —NH$_2$, —NHR$^1$, —N(R$^1$)$_2$, —CO$_2$H, —CO$_2$R$^1$, —CONH$_2$, —CONHR$^1$, —CON(R$^1$)$_2$, —CONHNH$_2$, or —OR$^1$ wherein each R$^1$ is independently alkyl of from 1 to 5 carbon atoms. In addition, R can be where n,m,o=1–18; (CH$_2$)$_n$—R$^2$ (in which n=0–18), wherein R$^2$ is a variously substituted aromatic ring, preferably, a phenyl group, being substituted with one or more alkoxy groups, preferably methoxy or O(CH$_2$)$_m$CH$_3$, (in which m=0–18), or a combination thereof.

In the above descriptions, the terms are generally used according to their standard meanings. The term "alkyl" as used herein means a branched or unbranched, saturated or unsaturated, monovalent or divalent, hydrocarbon radical having from 1 to 20 carbons, including lower alkyls of 1–8 carbons such as methyl, ethyl, n-propyl, butyl, n-hexyl, and the like, cycloalkyls (3–7 carbons), cycloalkylmethyls (4–8 carbons), and arylalkyls. The term "alkoxy" refers to alkyl radicals attached to the remainder of the molecule by an oxygen, e.g., ethoxy, methoxy, or n-propoxy. The term "alkylthio" refers to alkyl radicals attached to the remainder of the molecule by a sulfur.

The term of "acyl" refers to a radical derived from an organic acid by the removal of the hydroxyl group. Examples include acetyl, propionyl, oleoyl, myristoyl.

These compounds can then be used in a variety of applications, e.g., as antigens, diagnostic reagents, or as therapeutics. Thus, the present invention also provides pharmaceutical compositions which can be used in treating a variety of conditions. The pharmaceutical compositions are comprised of compounds which comprise a sialyl galactoside unit. Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527–1533 (1990).

The pharmaceutical compositions are intended for parenteral, intranasal, topical, oral or local administration, such as by aerosol or transdermally, for prophylactic and/or therapeutic treatment. Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the sialyl galactosides of the invention can be incorporated into liposomes formed from standard vesicle-forming lipids. A variety of methods are available for preparing liposomes, as described in, e.g., Szoka et al., *Ann. Rev. Biophys. Bioeng.* 9:467 (1980), U.S. Pat. Nos. 4, 235,871, 4,501,728 and 4,837,028. The targeting of liposomes using a variety of targeting agents (e.g., the sialyl galactosides of the invention) is well known in the art. (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized sialyl galactosides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion which is firmly embedded and anchored in the membrane. It must also have a reactive portion which is chemically available on the aqueous surface of the liposome. The reactive portion is selected so that it will be chemically suitable to form a stable chemical bond with the targeting agent or carbohydrate which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the nature and severity of the disease and the weight and general state of the patient, but generally range from about 0.5 mg to about 2,000 mg of sialyl galactoside oligosaccharide per day for a 70 kg patient, with dosages of from about 5 mg to about 200 mg of the compounds per day being more commonly used.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight, but generally range from about 0.5 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the sialyl galactoside of this invention sufficient to effectively treat the patient.

The compounds may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

The sialyl galactoside of the invention can be used as an immunogen for the production of monoclonal or polyclonal antibodies specifically reactive with the compounds of the invention. The multitude of techniques available to those skilled in the art for production and manipulation of various immunoglobulin molecules can be used in the present invention. Antibodies may be produced by a variety of means well known to those of skill in the art.

The production of non-human monoclonal antibodies, e.g., murine, lagomorpha, equine, etc., is well known and may be accomplished by, for example, immunizing the animal with a preparation containing the sialyl galactoside of the invention. Antibody-producing cells obtained from the immunized animals are immortalized and screened, or screened first for the production of the desired antibody and then immortalized. For a discussion of general procedures of monoclonal antibody production see Harlow and Lane, *Antibodies, A Laboratory Manual* Cold Spring Harbor Publications, N.Y. (1988).

The following examples are offered solely for the purposes of illustration, and are intended neither to limit nor to define the invention.

EXAMPLE 1

This example illustrates the general procedure for enzymatic sialylation using phosphoenolpyruvate (PEP), for the preparation of the saccharides below. The broad applicability of the present method is exemplified by sections 1.5 and 1.6 in which substrates are used which are not natural substrates for the enzymes.

1.1 Ethyl (Sodium 5-acetamido-3,5-dideoxy-α-D-glycero-D-galacto-2-nonulopyranosonate)-(2-3)-O-(β-D-galactopyranosyl)-(1-4)-O-β-D-gluco pyranoside.

The pH of a solution of phosphoenolpyruvate tri-sodium salt (3.16 g, 14 mmoles), with HEPES (1M, pH 7.4, 20 mL) and water (80 mL) was adjusted to 7.4 with 1 M NaOH. Ethyl β-D-galactopyranosyl-(1-4)-O-β-D-glucopyranoside (2.0 g, 5.4 mmoles), sialic acid (2.0 g, 6.5 mmoles), CMP (30 mg), ATP (10 mg) and MnCl$_2$ (0.36 g) were then added and the pH of the solution was readjusted to 7.4 with NaOH. Myokinase (500 U), pyruvate kinase (800 U), CMP-NeuAc synthetase (40 U) and α2,3-sialyl transferase (20 U) were then added and the reaction proceeded for 2 days. Additional MnCl$_2$ (0.5 g) was then added and the pH was adjusted to 7.4. After an additional 5 days, the solution was filtered and the filtrate was adsorbed onto silica gel. The resulting mixture was chromatographed (silica, methanol/ethyl acetate/acetic acid/water; 70/40/1.3/5) and the appropriate fractions were concentrated. The residue was again chromatographed (silica, methanol/ethyl acetate/water; 7/4/3) to afford a solid after concentration. The solid was dissolved in water (20 mL) and the pH was adjusted to 7.4 with 1 M NaHCO$_3$. The resulting solution was chromatographed (SEPHADEX® G-25, 20% ethanol/water), the appropriate fractions were concentrated and the solid was redissolved in water and lyophilized to afford 1.4 g (38%) of pure product as a white solid, R$_f$=0.42 (silica, 2-propanol/1M NH$_4$OAc; 8/2). In this reaction, a conversion of 100% was accomplished as evidenced by tlc.

1.2 Benzyl (Sodium 5-acetamido-3,5-dideoxy-α-D-glycero-D-galacto-2-nonulopyranosonate)-(2-3)-O-(β-D-galactopyranosyl)-(1-4)-O-β-D-gluco pyranoside.

The enzymatic reaction was carried out as described above, substituting benzyl β-D-galactopyranosyl-(1-4)-O-β-D-glucopyranoside for ethyl β-D-galactopyranosyl-(1-4)-O-β-D-glucopyranoside. The enzymatic reaction mixture was filtered and the filtrate was chromatographed (C-18 silica, water then 2% CH$_3$OH/H$_2$O) to afford 2.07 g (40%) of a white solid after lyophilization, R$_f$=0.45 (silica, 2-propanol/1M NH$_4$OAc 8/2). $^1$H NMR (300 MHz, D$_2$O) δ 7.35–7.41 (m, 5H, benzyl), 4.84 (d, J=11 Hz, 1H, benzyl), 4.70 (d, J=11 Hz, 1H, benzyl), 4.50 (d, J=8 Hz, 1H, H-1 galactose), 4.70 (d, J=9 Hz, 1H, H-1 Glc), 4.07–4.03 (dd, J=10, 3 Hz, 1H, H-3 Gal), 3.97–3.47 (m, 17H), 3.32–3.26 (t, 1H), 2.70 (dd, J=12, 5 Hz, 1H, H-3$_{eq}$ SA), 1.97 (s, 3H, NAc), 1.74 (dd, J=12, 12 Hz, 1H, H-3$_{ax}$ SA).

1.3 Sodium (5-acetamido-3,5-dideoxy-α-D-glycero-D-galacto-2-nonulopyranosonate)-(2-3)-O-(β-D-galactopyranosyl)-(1-4)-O-D-fructofuranose (sialyl lactulose).

The enzymatic reaction was carried out as described above, substituting β-D-galactopyranosyl-(1-4)-O-D-fructofuranose for ethyl β-D-galactopyranosyl-(1-4)-O-β-D-glucopyranoside. The enzymatic reaction mixture was filtered and the filtrate concentrated. The residue was chromatographed (silica, CH$_3$OH/ethyl acetate/water 7/4/3) to afford solid which was dissolve in water (20 mL) and the pH adjusted to 7.4 with NaHCO$_3$. This solution was chromatographed (SEPHADEX® G-25, 20% ethanol/water) to afford 1.5 g (78%) of a white solid after lyophilization, R$_f$=0.24 (silica, 2-propanol/conc NH$_4$OH/water 7/1/2). $^1$H NMR (300 MHz, D$_2$O) δ 4.64 (d, J=8 Hz, 1H, H-1 Gal), 4.54 (d, J=8 Hz, H-1), 4.32–3.48 (m, 20H), 2.75 (dd, J=11, 4 Hz, 1H, H-3eq SA), 2.02 (s, 3H, NAc), 1.75 (dd, J=12, 12 Hz, H-3ax SA).

1.4 Sodium (5-acetamido-3,5-dideoxy-α-D-glycero-D-galacto-2-nonulo-pyranosonate)-(2-3)-O-(α-D-galactopyranosyl)-(1-6)-O-D-glucopyranose (sialyl melibiose).

The enzymatic reaction, utilizing melibiose as the acceptor, was set up as described above except that HEPES was not added. Every 24 h for 3 days additional MnCl$_2$ (0.297 g) was added and the pH was adjusted to 7.4. On day 4, the pH was adjusted to 7.4 and by day five the reaction had stopped. Additional enzymes (as above) PEP (1.7 g) and MnCl$_2$ (0.297 g) were added and the pH adjusted to 7.4.

Every 24 h for 7 days the pH was adjusted to 7.4 at which time the reaction mixture was filtered and the filtrate concentrated and adsorbed to silica gel. Chromatography (silica, methanol/ethyl acetate/acetic acid/water 70/40/1.3/5) and appropriate fractions were concentrated. The residue was chromatographed (silica, methanol/ethyl acetate/water 7/4/3) to afford a solid after concentration. This solid was dissolved in water (20 mL) and the pH adjusted to pH of 7.4 with 1 M NaHCO$_3$. This solution was chromatographed (SEPHADEX® G-25, 20% ethanol/water), the appropriate fractions concentrated and the solid redissolved in water and lyophilized to afford 0.39 g (20%) of a white solid, $R_f$=0.38 (silica, 2-propanol/conc NH$_4$OH/water 7/1/2). $^1$H NMR (300 MHz, D$_2$O) δ 5.19 (d, J=4 Hz, H-1$_a$ Gal), 4.90 (d, J=3 Hz, 1H, H-1 Gal), 4.63 (d, J=8 Hz, H-1$_b$ Gal), 4.36–4.29 (dd, J=10, 3 Hz, 1H, H-3 Gal), 3.98–3.38 (m, 17H), 3.38–3.23 (m, 1H), 2.68 (dd, J=12, 5 Hz, 1H, H-3$_{eq}$ SA), 1.98 (s, 3H, NAc), 1.76 (dd, J=12, 12 Hz, 1H, H-3$_{ax}$ SA).

1.5 Sodium (5-acetamido-3,5-dideoxy-α-D-glycero-D-galacto-2-nonulo-pyranosonate)-(2-3)-O-(α-D-galactopyranosyl)-(1-6)-O-(α-D-galacto-pyranosyl)-(1-6)-O-(α-D-glucopyranosyl)-(1-2)-O-β-D-fructofuranoside (sialyl stachyose).

The enzymatic reaction, utilizing stachyose as the acceptor, was set up as described above except that HEPES was not added. Every 24 h for 3 days additional MnCl$_2$ (0.297 g) was added and the pH was adjusted to 7.4. On day 4, the pH was adjusted to 7.4 and by day five the reaction had stopped. Additional enzymes (as above) PEP (1.7 g) and MnCl$_2$ (0.297 g) were added and the pH adjusted to 7.4. Every 24 h for 21 days the pH was adjusted to 7.4 at which time the reaction mixture was filtered and the filtrate chromatographed (SEPHADEX® G-25, 20% ethanol/water), the appropriate fractions were concentrated and the solid redissolved in water and lyophilized to afford 0.156 g (5%) of a white solid, $R_f$=0.17 (silica, 2-propanol/conc NH$_4$OH/water; 7/1/2). $^1$H NMR (300 MHz, D$_2$O) δ 5.37 (d, J=4 Hz, 1H, H-1), 4.96 (d, J=4 Hz, 1H, H-1), 4.94 (d, J=4 Hz, 1H, anomeric), 4.38–4.24 (dd, J=10, 3 Hz, 1H, H-3 Gal), 4.16–3.48 (m, 31H), 2.68 (dd, J=12, 5 Hz, H-3$_{eq}$ SA), 1.98 (s, 3H, NAc), 1.76 (dd, J=12, 12 Hz, H-3$_{ax}$ SA).

1.6 Sodium (5-acetamido-3,5-dideoxy-α-D-glycero-D-galacto-2-nonulo-pyranosonate)-(2-3)-O-(α-D-galactopyranosyl)-(1-6)-O-(α-D-gluco-pyranosyl)-(1-2)-O-β-D-fructofuranoside (sialyl raffinose).

The enzymatic reaction, utilizing raffinose as the acceptor, was set up as described above except that HEPES was not added. Every 24 h for 3 days additional MnCl$_2$ (0.297 g) was added and the pH was adjusted to 7.4. On day 4, the pH was adjusted to 7.4 and by day five the reaction had stopped. Additional enzymes (as above) PEP (1.7 g) and MnCl2 (0.297 g) were added and the pH adjusted to 7.4. Every 24 h for 4 weeks the pH was adjusted to 7.4. The reaction mixture was then filtered and the filtrate chromatographed (silica, methanol/ethyl acetate/acetic acid/water; 70/40/1.3/5) and appropriate fractions were concentrated. The residue was dissolved in water (20 mL) and the pH adjusted to 7.4 with NaHCO$_3$. This solution was chromatographed (SEPHADEX® G-25, 20% ethanol/water), the appropriate fractions concentrated and the solid was redissolved in water and lyophilized to afford 0.112 g (5%) of a white solid, $R_f$=0.29 (silica, 2-propanol/conc NH$_4$OH/water 7/1/2). $^1$H NMR (300 MHz, D$_2$O) δ 5.37 (d, J=3.7 Hz, 1H, H-1), 4.96 (d, J=3.7 Hz, 1H, H-1), 4.29 (dd, J=10.3, 2.8 Hz, 1H, H-3 Gal), 4.17 (d, J=8.8 Hz, 1H), 4.04–3.52 (m, 25H), 2.68 (dd, J=4.7, 12.2 Hz, 1H, H-3 SA), 1.97 (s, 3H, NHAc), 1.76 (dd, J=12.2, 12.2 Hz, 1H, H-3 SA).

EXAMPLE 2

This example illustrates the synthesis of sodium (5-acetamido-3,5-dideoxy-α-D-glycero-D-galacto-2-nonulopyranosonate)-(2-3)-O-(β-D-galactopyranosyl)-(1-3)-O-D-arabinose.

The pH of a solution of 3-O-β-D-galactopyranosyl-D-arabinose (0.911 g, 2.92 mmol), sialic acid (0.993 g, 3.5 mmol), CTP disodium salt (2.3 g, 4.38 mmol), MnCl$_2$ (0.6 g) and water (50 mL) was adjusted to 8.0 and the CMP-NeuAc synthetase (30 U) and sialyl transferase (20 U) were added. The pH was carefully monitored and maintained between 7.2–7.8 by the addition of 1N NaOH. After 3 h, the pH of the solution dropped slowly and the reaction mixture was allowed to sit for 18 h. Additional MnCl$_2$ (0.6 g) was then added and the pH was adjusted to 7.5 with 1N NaOH. Every 24 hr for the next 5 days the pH was readjusted to 7.5. The reaction was complete as observed by TLC and was then filtered. The filtrate was concentrated to dryness with silica gel and the solid was chromatographed (silica, methanol/ethyl acetate/acetic acid/water; 70/40/1.5/5) and concentration of appropriate fractions provided a solid. This material was chromatographed (silica, methanol/ethyl acetate/water; 7/4/3) to afford a solid which was dissolved in water (20 mL) and the pH adjusted to pH of 7.4 with sat. NaHCO$_3$. This solution was chromatographed (SEPHADEX® G-25, 20% ethanol/water), the appropriate fractions concentrated and the solid redissolved in water and lyophilized to afford 0.755 g (41%) of white solid, $R_f$=0.30 (silica, 2-propanol/conc NH$_4$OH/water; 7/1/2). $^1$H NMR (300 MHz, D$_2$O) δ 5.22 (d, J=2 Hz, H-1), 4.57 (d, J=8 Hz, 1H, H-1 Gal), 4.48 (d, J=8 Hz, 1H, H-1), 4.15–3.52 (m, 18H), 2.73–2.68 (dd, J=12, 3 Hz, 1H, H-3$_{eq}$ SA), 1.97 (s, 3H, NAc), 1.74 (dd, J=12, 12 Hz, 1H, H-3$_{ax}$ SA).

EXAMPLE 3

This example illustrates the production of α-N-acetylneuraminic acid(2,3)β-galactosyl(1,4)glucose using the sialyl transferase cycle with control of the manganese ion concentration.

In a polypropylene vessel, phosphoenolpyruvate trisodium salt (285.4 g, 1.22 mol) and sialic acid (197 g, 0.637 mol) were dissolved in 5 L of water and the pH was adjusted to 7.1 with 6 M NaOH. Cytidine-5'-monophosphate (5.14 g, 15.9 mmol) and potassium chloride (7.9 g, 0.106 mol) were added and the pH was re-adjusted to 7.45 with 6 M NaOH. Pyruvate kinase (28,000 units), myokinase (17,000 units), adenosine triphosphate (0.98 g, 1.6 mmol), CMP NeuAc synthetase (1325 units), α2,3 sialyltransferase (663 units) and MnCl$_2$.4H$_2$O (52.4 g, 0.265 mol) were added and mixed. To a 3.7 L portion of the resulting mixture was added lactose (119 g, 0.348 mol) and sodium azide (1.75 g). The reaction mixture was kept at room temperature and monitored daily by thin layer chromatography (tlc) and ion chromatography. After two days, additional enzymes were added as follows: pyruvate kinase (38,100 units), myokinase (23,700 units), CMP NeuAc synthetase (935 units), and α2,3 sialyltransferase (463 units). The pH was periodically adjusted to 7.5 with 6 M NaOH. Additionally, the manganese ion concentration was measured and supplemented as shown in the table below.

TABLE

| Day | [Mn++] (measured, mM) | Loss of Mn++ (from previous day) | Amount Supplemented (mL of 1M, final added conc) |
|---|---|---|---|
| 1 | 28 | 22.0 | none |
| 2 | 23.9 | 4.1 | none |
| 3 | 10.7 | 13.2 | 111 mL, +30 mM |
| 4 | 1.4 | 39.3 | 111 mL, +30 mM |
| 5 | 3.0 | 28.4 | 148 mL, +40 mM |
| 6 | 12.9 | 30.1 | 74 mL, +20 mM |
| 7 | 10.0 | 22.9 | 80 mL, +20 mM |
| 8 | 12.0 | 18.0 | 80 mL, +20 mM |
| 9 | 24.3 | 7.7 | none |

On day 9, the reaction was essentially complete by tlc. As the results in the table indicate, the depletion of Mn++ resulted in additional amounts of $MnCl_2 \cdot 4H_2O$ being added almost daily to maintain the metal ion concentration. Manganese ion is a required cofactor for at least one enzyme in the sialyl transferase cycle. However, the manganese ion and the inorganic phosphate produced (see FIG. 1) form a complex of very low solubility. Because of this limited solubility, the transferase cycle can continue to proceed, but at reduced reaction rates. By supplementing the manganese ions which are lost by precipitation with pyrophosphate, the rate of reaction can be maintained. Thus, when manganese ion concentration is maintained in an optimal range, the sialyl transferase reaction cycle can be driven to completion.

EXAMPLE 4

This example illustrates the workup and purification of the trisaccharide produced in Example 3 followed by peracetylation and esterification.

A solution (2 L) of sodium 5-acetamido-3,5-dideoxy-α-D-glycero-D-galacto-nonulopyranosylonate-(2-3)-O-β-D-galactopyranosyl-(1-4)-O-β-D-glucopyranose produced from the action of a sialyl transferase in the presence of the appropriate cofactors on lactose (55 g) was filtered through paper. The filtrate was run through a membrane with a 3000 or 10,000 molecular weight cut off to remove protein from the desired product. The eluate was concentrated and desalted by running it against a reverse osmosis membrane in a suitable apparatus (Millipore, Bedford, Mass.). The retentate containing the product was evaporated to a thick syrup. Optionally the retentate can be treated with a chelating resin to remove divalent cations. After filtration the filtrate contained the desired product substantially free of salts and in a high state of purity as shown by $^1$Hmr spectroscopy. Otherwise the syrup was so evaporated twice with pyridine (2×200 mL). The evaporation flask was charged with a solution of N,N-dimethylaminopyridine (2.2 g) in pyridine (1.2 L). Acetic anhydride (0.83 L) was added during a period of 1 hour. The resulting mixture was left for 24–48 hours rotating slowly at room temperature. The reaction is checked by TLC (methanol:dichloromethane 1:9). Upon complete reaction vacuum is applied and the solution is evaporated to give a residue.

The residue was dissolved in ethyl acetate (1.5 L). This solution was washed with 5% aqueous hydrochloric acid (1.5 L) followed by saturated aqueous sodium bicarbonate (1.5 L) and finally water (1.5 L). The organic layer was dried over anhydrous sodium sulfate and filtered. The filtrate was concentrated to a semi-solid residue. The per-O-acetylated lactone trisaccharide (69 g) was dissolved in methanol (350 mL) and a sodium methoxide solution (17.5 mL, 25% solution in methanol) was added followed by water (3.5 mL). When TLC developed with isopropanol:ammonium hydroxide:water 7:1:2 showed the reaction to be complete acetic acid (2 mL) was added to the solution. Ethyl ether (180 mL) was added to the solution to precipitate the product. This solid was filtered and dissolved in water (350 mL). Charcoal (24 g) was added to this solution and heated to 60° C. for one hour. This solution was allowed to cool to ambient temperature and filtered. Evaporation of the filtrate gave the solid product (34 g). $^1$Hmr spectroscopy showed this solid to be pure sialyl lactose containing 11% sodium acetate weight by weight.

EXAMPLE 5

This example provides another workup and purification of the trisaccharide produced in Example 3.

About 50 mL of the enzyme reaction mixture from above Example 3 was adsorbed onto silica gel and chromatography (silica, methanol/ethyl acetate/acetic acid/water; 70/40/1.3/5) was performed. Appropriate fractions were concentrated and re-chromatographed (silica, methanol/ethyl acetate/water; 7/4/3) to afford a solid after concentration. This solid was dissolved in water (20 mL) and the pH was adjusted to pH of 7.4 with 1 M $NaHCO_3$. This solution was chromatographed (SEPHADEX® G-25, 20% ethanol/water), the appropriate fractions concentrated and the solid redissolved in water and lyophilized to afford 1.4 g of pure sialyl lactose.

All publications, patents and patent applications mentioned in this specification are herein incorporated by reference into the specification to the same extent as if each individual publication, patent or patent application was specifically and individually indicated to be incorporated herein by reference.

The above description is illustrative and not restrictive. Many variations of the invention will become apparent to those of skill in the art upon review of this disclosure. Merely by way of example a number of substrates, enzymes, and reaction conditions can be substituted into the glycosyl transferase cycles as part of the present invention without departing from the scope of the invention. The scope of the invention should, therefore, be determined not with reference to the above description, but instead should be determined with reference to the appended claims along with their full scope of equivalents.

What is claimed is:

1. A method for sialylating an acceptor sugar, comprising:
   (a) providing a reaction medium comprising:
      (i) a sialyl transferase;
      (ii) a catalytic amount of a CMP-sialic acid synthetase;
      (iii) a sialic acid;
      (iv) an acceptor sugar for said sialyltransferase;
      (v) CTP; and
      (vi) a soluble divalent metal cation; and
   (b) adding sufficient divalent metal cation to said reaction medium to restore a portion of said divalent cation lost during the course of the reaction to thereby achieve or maintain a concentration of said divalent metal cation in said reaction medium between about 1 mM and about 75 mM, and wherein step (b) occurs without interruption of said sialylating reaction.

2. A method in accordance with claim 1, wherein said reaction medium further comprises a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP.

3. A method in accordance with claim 1, wherein said supplementing is discontinuous.

4. A method in accordance with claim 1, wherein said supplementing is continuous.

5. A method in accordance with claim 1, wherein said soluble divalent metal cation is a member selected from the group consisting of $Mn^{++}$, $Mg^{++}$, $Mg^{++}$, $Ca^{++}$, $Co^{++}$, $Zn^{++}$ and combinations thereof.

6. A method in accordance with claim 1, wherein said sialyltransferase is $\alpha(2,3)$sialyltransferase.

7. A method in accordance with claim 1, wherein said sialyltransferase is $\alpha(2,6)$sialyltransferase.

8. A method in accordance with claim 1, wherein said sialyltransferase is $\alpha(2,3)$sialyltransferase and said soluble divalent metal cation is $Mn^{++}$.

9. A method in accordance with claim 1, wherein said sialic acid is 5-N-acetylneuraminic acid.

10. A method in accordance with claim 1, wherein said acceptor is lactose.

11. A method in accordance with claim 1, wherein said sialic acid is 5-N-acetylneuraminic acid and said acceptor is lactose.

12. A method in accordance with claim 2, wherein said sialic acid is 5-N-acetylneuraminic acid, said acceptor is lactose, said nucleoside triphosphate is ATP, said phosphate donor is acetyl phosphate, said kinase is acetate kinase, said nucleoside monophosphate kinase is myokinase, said soluble divalent metal cation is $Mn^{++}$ and said sialyltransferase is $\alpha(2,3)$sialyltransferase.

13. A method in accordance with claim 2, wherein said sialic acid is 5-N-acetylneuraminic acid, said acceptor is lactose, said nucleoside triphosphate is ATP, said phosphate donor is acetyl phosphate, said kinase is acetate kinase, said nucleoside monophosphate kinase is myokinase, said soluble divalent metal cation is $Mn^{++}$ and said sialyltransferase is $\alpha(2,3)$sialyltransferase.

14. A method in accordance with claim 1, wherein said reaction medium further comprises a buffer to maintain said reaction medium at a pH value of about 6 to about 8.

15. A method for the enzymatic formation of sialyl$\alpha$2→3$\beta$galactoside, comprising:
(a) combining the following components in a single vessel to form a reaction mixture:
(i) a catalytic amount of an $\alpha(2,3)$sialyltransferase;
(ii) a catalytic amount of a CMP-sialic acid synthetase;
(iii) a sialic acid;
(iv) an acceptor for said $\alpha(2,3)$sialyltransferase having a galactosyl unit;
(v) a CMP-sialic acid recycling system comprising at least 2 moles of phosphate donor per each mole of sialic acid, and catalytic amounts of a nucleoside triphosphate, cytidine monophosphate, a kinase capable of transferring phosphate from said phosphate donor to a nucleoside diphosphate, and a nucleoside monophosphate kinase capable of transferring the terminal phosphate from a nucleoside triphosphate to CMP; and
(vi) a reaction medium containing a soluble divalent metal cation in an amount of from about 1 mM to about 75 mM and having a pH value of about 6 to 8;
(b) maintaining said reaction mixture at a temperature of about 0° C. to about 45° C.; and
(c) adding sufficient divalent metal cation to said reaction medium to restore a portion of said divalent cation lost during the course of the reaction to thereby achieve or maintain a concentration of said divalent metal cation in said reaction medium between about 1 mM and about 75 mM, and wherein step (d) occurs without interruption of formation of said sialyl2$\alpha$→3$\beta$galactoside.

16. A method in accordance with claim 15, wherein said soluble divalent metal cation is a member selected from the group consisting of $Mn^{++}$, $Mg^{++}$, $Ca^{++}$, $Co^{++}$, $Zn^{++}$ and combinations thereof.

17. A method in accordance with claim 15, wherein the soluble divalent metal cation is $Mn^{++}$.

18. A method in accordance with claim 15, wherein said sialic acid is 5-N-acetyl-neuraminic acid.

19. A method in accordance with claim 15, wherein said acceptor is lactose.

20. A method in accordance with claim 15, wherein said sialic acid is 5-N-acetyl-neuraminic acid and said acceptor is lactose.

21. A method in accordance with claim 15, further comprising recovering said formed sialyl $\alpha$2→3$\beta$galactoside.

22. A method in accordance with claim 21, wherein said recovering comprises membrane filtration of a solution of sialyl $\alpha$2→3$\beta$galactoside, said membrane having a molecular weight cutoff of about 100 to about 10000.

23. A method in accordance with claim 21, wherein said recovering comprises membrane filtration of a solution of sialyl $\alpha$2→3$\beta$galactoside, said membrane having a molecular weight cutoff of about 200 to about 1000.

24. A method in accordance with claim 21, wherein said recovering comprises nanofiltration of a solution of sialyl $\alpha$2→3$\beta$galactoside.

25. A method in accordance with claim 15, wherein said sialic acid is 5-N-acetylneuraminic acid, said acceptor is lactose, said nucleoside triphosphate is ATP, said phosphate donor is phosphoenolpyruvate, said kinase is pyruvate kinase, said nucleoside monophosphate kinase is myokinase and said soluble divalent metal cation is $Mn^{++}$.

26. A method in accordance with claim 15, wherein said sialic acid is 5-N-acetylneuraminic acid, said acceptor is lactose, said nucleoside triphosphate is ATP, said phosphate donor is acetyl phosphate, said kinase is acetate kinase, said nucleoside monophosphate kinase is myokinase and said soluble divalent metal cation is $Mn^{++}$.

* * * * *